United States Patent [19]

He et al.

[11] Patent Number: 5,783,410

[45] Date of Patent: Jul. 21, 1998

[54] BACTERIA IDENTIFICATION METHOD AND APPARATUS

[75] Inventors: Lin He, 3 Dongnenbei Rd, Shenzhen City, Guangdong 518001; Qiuming Liu, Guangdong; Baoduo Liang, Guangdong; Jinliang Wang, Tianjin, all of China

[73] Assignee: Lin He, Guangdong, China

[21] Appl. No.: 569,210

[22] PCT Filed: Jun. 14, 1994

[86] PCT No.: PCT/CN94/00044

§ 371 Date: May 28, 1996

§ 102(e) Date: May 28, 1996

[87] PCT Pub. No.: WO94/29480

PCT Pub. Date: Dec. 22, 1994

[30] Foreign Application Priority Data

Jun. 14, 1993 [CN] China ............................ 93 1 06932.7
Jun. 14, 1993 [CN] China ............................ 93 1 06931.9

[51] Int. Cl.$^6$ ............................ C12Q 1/04; C12Q 1/34; C12Q 1/54
[52] U.S. Cl. ............................ 435/34; 435/14; 435/18; 435/21; 435/25; 435/12; 435/822; 435/4; 422/50; 422/68.1
[58] Field of Search ............................ 435/34, 14, 18, 435/21, 25, 12, 822, 4; 422/50, 68.1

[56] References Cited

U.S. PATENT DOCUMENTS

| 4,453,220 | 6/1984 | Flegal et al. ............... 364/413 |
| 4,526,865 | 7/1985 | Silman ............... 435/35 |
| 4,767,702 | 8/1988 | Cohenford ............... 435/24 |
| 5,096,668 | 3/1992 | Thompson ............... 422/58 |
| 5,185,859 | 2/1993 | Guttag et al. ............... 395/164 |

FOREIGN PATENT DOCUMENTS 1073720A  6/1993  China.

*Primary Examiner*—Louise Leary
*Attorney, Agent, or Firm*—Merchant, Gould, Smith, Edell, Welter & Schmidt, P.A.

[57] ABSTRACT

The present invention discloses a bacteria-coding identification method, bacteria biochemical properties identifying papers which detect the biological properties using this method, and apparatus or means useful for identifying the genus and species of bacteria using the coding identification method and biochemical properties-identifying papers.

6 Claims, 2 Drawing Sheets

BACTERIA IDENTIFICATION METHOD AND APPARATUS

FIELD OF THE INVENTION

The invention involves a bacteria-coding identificaton method, which is for parenteral gram-negative bacilli, enteric gram-negative bacilli, Enterobacteriaceae bacteria, anaerobic bacteria, neisseria/hemophilus, campylobacter, yeast-like fungi, corynebacteria, Micrococcaceae bacteria, Streptoccaceae bacteria, bacilli and lactobacilli, and bacteria biochemical properties-identifying papers which detect the biological properties using this method, i.e. identification papers for parenteral gram-negative bacilli, enteric gram-negative bacilli, Enterobacteriaceae bacteria, anaerobic bacteria, neisseria/hemophilis, campylobacter, yeast-like fungi, corgnebacteria, Micrococcaceae bacteria, Streptoccaceae bacteria, bacilli and lactobacilli, and apparatus or means useful for identifying the genus and species of bacteria using the coding identification method and biochemical properties-identifying papers.

BACKGROUND OF THE INVENTION

Bacteria ideatification is a course including detecting the biological properties of the strain to be identificated using the bacteria biological properties assay device, and then according to the detection results of the biological properties of the strain, determining its genus and species by identification method and with the help of identification apparatus or identification coding retrieval means. At present, there are two kinds of bacteria identification met , which are double-branch identification and numerical identification, The former, which is well-known, achieves the identification of genus and species of the stain to be identified by analyzing the detection results of the biological properties one by one. The method contains too many identification steps and costs a lot time because the assay route and the next item of biological property to be detected cannot be determined until the detection result of the former one has been obtained and the steps are repeated again and again until the identification conclusion can be drawn. Meanwhile, the method Can not provide probability parameter when the bacteria identification result is shown because it is logical reasoning analytics. In order to decrease steps and reduce time, scholars abroad put forward numerical identification methods in succession, such as differentiation analysis method, nearest neighbor analysis method, Ochireed distance method, related coefficient method, probability most approximate value model method et. al.

These methods can simultaneously analyse several detection results of the biological properies of the strain to be identifed, which are obtained at one time, and provide probability parameter when the bacteria identification result is shown. Among the methods, probability most approximate value model identification method is applied at most and its effect is beat. Numerical identification methods, including probability most approximate value model method, are also called coding identification methods because in the course of bacteria identification by numerical methods several biological properties of bacteria usually need to be detected and the detection items or detection results need to be coded. There are 15 to 32 coding test items or sorts of test medium in the paper-hole respectively in the well-known coding identification methods or bacteria biochemical properties-identifying papers, such as VITEK, ATB, API, Micro-ID and Entertube II et al. Because of the unreasonable selection and inferior combination effect of the coding test items or the test medium sorts in the hole of bacteria biochemical properties-identifying papers, the identification of the bacteria identified for group is inefficient. Because the amount o coding test items or the medium sorts of biochemical properties-identifying papers is large and pats of coding test items have not identification value to identifying bacteria for group in the combination, the consumption and waste is age.

Different identification apparatus o identification coding retrieval means is used in the course of bacteria identification besides the use of different identification methods and bacteria biochemical properties-identifying papers. At present, bacteria identification device has special bacteria identifier with microprocessor as the core component and computer supported by bacteria identification software system. The well-known special bacteria identifier, such as VITEK Microbiological Automated Analyzer (VITEK Inc. U. S. A.) and ATB Bacteria Identifier (bio Merieux Inc., France), and computer supported by bacteria identification software system, such as API Advisory Computer, which identify bacteria by VITEK, ATB and API coding identification method respectively, exist the intrinsic defects of VITEK, ATB and API coding identification method mentioned above. Because the storage mediums of identification software are hard disc, floppy disc or tape, they have poor stability, physical vulnerability, complicated structure of themselves and the interface between them and microprocessor and large volume. Because there is no simulated color image on detection results of bacteria biological properties in the identification device, the man-machine interface is not visual and the operator can not obtain contrast promptness or analysis. Because there are less units of bacteria that can be identified in the identification device, the range of bacteria identification is narrow. Because the type of test system to detect the biological properties of the bacteria to be identified in ed in the identification system is single, the application is limited. Because there are many components in the identification device and the structure and interface are complicated, the volume is large, the cost of manufacture is high and the maintenance and upkeep are inconvenient. The well-known bacteria identification coding retrieval means, such as API Identification Coding Retrieval Manual and Micro-ID Identification Coding Retrieval Manual and the bacteria identification coding cetrieval computers which identity bacteria by API and Micro-ID coding identification method respectively, exist the intrinsic defects of API and Micro-ID coding identification method mentioned above.

SUMMARY OF THE INVENTION

The object of the present invention is to provide a bacteria-coding identification method, which is for parenteral gram-negative bacilli, enteric gram-negative bacilli, Enterobacteriaceae bacteria, anaerobic bacteria, neisseria/hemophilus, campylobacter, yeast-like fungi, corynebacteria, Micrococcaceae bacteria, Streptoccaceae bacteria, bacilli and lactobacilli, and bacteria biochemical properties-identifying papers which detect the biological properties using this method, i. e. identification papers for parenteral gram-negative bacilli, enteric gram-negative bacilli, Enterobacteriaceae bacteria, anaerobic bacteria, neisseria/hemophilus, campylobacter, yeast-like fungi, corynebacteria, Micrococcaceae bacteria, Steptoccaceae bacteria, bacilli and lactobacilli, and apparatus or mean useful for identifying the genus and species of bacteria using the coding identification method and biochemical properties-identifying papers.

The above object of the present invention is realized in this way: First, according to the known bacteria biological properties, the coding test items for bacteria Identification are selected by optimum seeking method. Thereafter, bacteria biochemical properties-identifying papers are preparated on the basis of the optimum coding test items and are used to detect the biochemical properties of the strain to be identified. The detected bacteria biochemical properties are coed as biological code according to the method of 4-2-1 or 1-2-4 in octonal notation. Then the, identification conclusion on the genus and species of the strain to be identified is drawn from biological code by using numeral identification method and with the help of bacteria identification apparatus or by using bacteria identification coding retrieval means, which is obtained through procoding the probable test presentation or biological code of known bacteria in bacteria identification coding test items. To identify bacteria in different groups, the coding test items, the medium sorts of biochemical test in biochemical properties-identifying papers and the coding method of biological code are as the follows.

(1) To identify parenteral gram-negative bacilli, the coding test items and the mediums in the paper-holes of biochemical properties-identifying papers are 15 kinds of assimilation tests and test mediums, which are those of 2-keto-gluconate (2 KG), 3-hydroxy-benzoate (3HB), 3-hydroxy-butyrate (OBU), citrate (CIT), L-proline (LPR), histose (HIS), N-acetyl-D-glucosamine (NAG), glycogen (GLY), maltose (MA), sucrose (SUC), D-melibiose (MEL), L-fucose (FUC), D-glucose (GLU), inositol (IND) and manitol (MAN). The coding method is as follows.

| Coding Method | 2KG + 2HB − OBU + | CIT + LPR − HIS − | NAG − GLY + MAL + | SUC − MEL − FUC + | GLG + IND + MAN + | Biological Code |
|---|---|---|---|---|---|---|
| 4-2-1 | 5 | 4 | 3 | 0 | 7 | 64807 |
| 1-2-4 | 6 | 1 | 6 | 0 | 7 | 61607 |

(2) To identify enteric gram-negative bacilli, the coding test items ate 15 tests, which are of those oxidase (OXI), growth in MCK agar (MCK), motility (MOT), lysine decarboxylase (LDC), ornithint decarboxylase (ODC), arginine dihydrolase (ADH), indole production (IND) urease (URE), citrate utilization (CIT), glucose oxidation (GLO), mannitol fermentation (MAN), sucrose fermentation (SUC), chamnose fermentation (RHA), amygdalin fermentation (AMY) arid sorbitol fermentation (SOR), the mediums in the paper-holes of biochemical properties-identifying papers are 12 sorts of test mediums, which are those of lysine decarboxylase (LDC), ornithint decarboxylase (ODC), arginine dihydrolase (ADH), indole production (IND), urease (URE), citrate utilization (CIT), glucose oxidation (GLO), mannitol fermentation (MAN), sucrose fermentation (SUC), chamnose fermentation (RHA), amygdalin fermentation (AMY) and sorbitol fermeatation (SOR). The coding method is as follows.

| Coding Method | OXI − MCK − MOT + | LDC − ODC + ADH − | IND + URE + CIT − | OFO + MAN + SUC + | RHA − AMY − SOR − | Biological Code |
|---|---|---|---|---|---|---|
| 4-2-1 | 1 | 2 | 6 | 7 | 0 | 12670 |
| 1-2-4 | 4 | 2 | 3 | 7 | 0 | 42370 |

(3) To identify Enterobacteriaceae bacteria, the coding test items and the mediums in the paper-holes of biochemical properties-identifying papers are 12 kinds of tests and test mediums, which are those of lysine decarboxylase (LDC), ornitine decarboxylase (ODC), malonate utilization (MAU), urease (URE), cellobiose fermentation (CEL), D-sorbitol fermentation (SOR), L-arabinose fermentation (LAR), adonitol fermentation (ADO), sucrose fermentation (SUC), dulcitol fermentation (DUL), α-methyl-D-glucoside fermentation (AMG) and D-mannitol fermentation (MAN). The coding method is as follows.

| Coding Method | LDC + ODC − MAU + | URE + CEL − SOR − | LAR − ADO + SUC + | DUL − AMG − MAN − | Biological Code |
|---|---|---|---|---|---|
| 4-2-1 | 5 | 4 | 3 | 0 | 6430 |
| 1-2-4 | 5 | 1 | 6 | 0 | 5160 |

(4) To identify anaerobic-bacteria, the coding test items are 14 tests which are those of gram stain (GRS), sporulation (SPO), α-glucoside (AGL), α-galactosidase (AGA), α-arabinosidase (AAR), β-glucosidase (BGL), β-galactosidase (BAG), β-glucuronidase (BGU), leucine arylamidase (LAA), proline arylamidase (PRA), alkaline phosphatase (ALP), indole production (IND), mannose fermentation (MAS) and β-N-acetyl-glucosaminidase (NAG), the mediums in the paper-holes of biochemical properties-identifying papers are 12 sorts of test mediums, which are those of α-glucosidase (AGL), α-galactosidase (AGA), α-arabinosidase (AAR), β-glucosidase (BGL), β-galactosidase (AGA), β-glucuronidase (BUG), leucine arylamidase (LAA), proline arylamidase (PRA), alkaline phosphatase (ALP), indole production (IND), mannose fermentation (MAS) and N-acetyl-β-D-glucosaminidase (NAG). The coding method is as follows:

| Coding Method | GRS + SPO − — | AGL − AGA − ARA − | BGL + BGA − BGU + | LAA − PRA + ALP + | IND − MAS + NAG − | Biological Code |
|---|---|---|---|---|---|---|
| 4-2-1 | 2 | 0 | 5 | 3 | 2 | 20532 |
| 1-2-4 | 1 | 0 | 5 | 6 | 2 | 10562 |

(5) To identify neisseria/hemophilus, the coding test items are 10 tests which are those of catalase (CAT), growth in Martin-Thayer medium (MTM), glucose fermentation (GLU), maltose fermentation (MLT), β-gluco-sidase (BGL), phenylphosphonate (OPS), glycine arylamidase (GLY), γ-glutamyl arylamidase (GGT), proline arylamidase (PRO) and reduction of resazurin (RES), the mediums in the paper-holes of biochemical properties-identifying papers are 9 sorts of test mediums, which are those of growth in Martin-Thayer medium (MTM), glucose fermeatation (GLU), maltose fermeatation (MLT), β-glucosidase (BGL), phenyl-phosphonate (OPS), glycine crylamidase (GLY), γ-glutamyl arylamidase (GGT), proline arylamidase (PRO) and reduction of resazurin (RES)-The coding method is as follows.

| Coding Method | CAT + — — | MTM + GLU − MLT − | BGL − OPS + GLY + | GGT − PRO − RES + | Biological Code |
|---|---|---|---|---|---|
| 4-2-1 | 1 | 4 | 3 | 1 | 1431 |
| 1-2-4 | 1 | 1 | 6 | 4 | 1164 |

(6) To itemdify campylobacter, the coding test items and the mediums in the paper-holes of biochemical properties-identifying papers are 9 kinds of test and test mediums, which are those of catalase (CAT), reduction of nitrate (NIT), urease (URE), succinate assimilation (SUT), acetate assimilation (ACE), hippurate hydrolysis (HIP) hydrogen sulfide production (HYS), γ-glutamyl transferase (GGT) and alkaline posphatase (ALP). The coding method is as follows.

| Coding Method | CAT+ NIT– URE– | SUC+ ACE– HIP+ | HYS– GGT+ ALP– | Biological Code |
|---|---|---|---|---|
| 4-2-1 | 4 | 5 | 2 | 452 |
| 1-2-4 | 1 | 5 | 2 | 152 |

(7) to identify yeast-like fungi, the coding test items and the mediums in the paper-holes of biochemical properties-identifying papers are 15 kinds of assimilation tests and test mediums, which are those of 2-keto -gluconate (2KG), actidione (ACT), erythritol (ERY), mannitol (MAN), inositol (INO), N-acetyl-glucosamine (NAG), L-arabinose (LAR), galactose (GAL), raffinose (RAF), cellobose (CEL), lactose (LAC), maltose (MAL), melibiose (MEL), trehalose (TRE) and esculin (ESC). The coding method is as follows.

| Coding Method | 2KG+ ACT– ERY– | MAN+ INO– NAG+ | LAR– GAL– RAF+ | CEL– LAC+ MAL+ | MEL– TRE+ ESC– | Biological Code |
|---|---|---|---|---|---|---|
| 4-2-1 | 4 | 5 | 1 | 3 | 2 | 45132 |
| 1-2-4 | 1 | 5 | 4 | 6 | 2 | 15462 |

(8) To identify corynebacteria, the coding test items and the mediums in the paper-holes of biochemical properties-identifying papers are 9 kinds of test and test mediums, which are those of reduction of nitrate (NIT), urease (URE), esculin hydrolysis (ESC), L-maltose fermentation (MAL), sucrose fermentation (SUC), ribose fermentation (RIB) lactose fermentation (LAC), α-glucosidase (AGL) and β-galactosidase (BOA). The coding method is as follows.

| Coding Method | NIT+ URE– ESC+ | MAL– SUC– RIB– | LAC– AGL+ BGA+ | Biological Code |
|---|---|---|---|---|
| 4-2-1 | 5 | 4 | 3 | 543 |
| 1-2-4 | 5 | 1 | 6 | 516 |

(9) To identify Micrococcaceae bacteria, the coding test items and the mediums in the paper-holes of biochemical properties-identifying papers are 12 kinds of tests and test mediums, which are those of urease (URE), reduction of nitate (NIT), 3-hydroxy-butanone production (HYB), are dihydrolase (ADH), ornithine decarboxylase (ODC), alkaline phosphatase (ALP), β-galactosidase (BGA), β-glucuronidase (BGU), glucose fermentation (GLF), sucrose fermentation (SUC), mannitol fermentation (MAN) and trehalose fermentation. The coding method is as follows.

| Coding Method | URE+ NIT+ HYB+ | ADH– ODC+ ALP+ | BGA+ BGU– GLF+ | SUC– MAN+ TRE– | Biological Code |
|---|---|---|---|---|---|
| 4-2-1 | 7 | 3 | 5 | 2 | 7352 |
| 1-2-4 | 7 | 6 | 5 | 2 | 7652 |

(10) To identify streptoccaceae bacteria, the coding test items are 13 tests which are those of hemolysis (HEM) 3-hydroxy-butanone production (HYB), hippurate hydrolysis (HIP), arginine dihydrolase (ADH), α-leucine arylamidase (LAA), β-glucuronidase (BGU), β-galactosidase (BGA), ribose fermentation (RIB), raffinose fermentation (RAF), sorbitol fermentation (SOR) L-arabinose fermentation (LAR) and trehalose fermentation (TRE), the mediums in the paper-holes of biochemical propeties-identifying papers are 12 sorts of test mediums, which are those of 3-hydroxy-butanone production (HYB), hippurate hydrolysis (HIP), arginine dihydrolase (ADH), α-leucine arylamidase (LAA), β-glucuronidase (BGU), β-galactosidase (BGA), ribose fermentation (RIB), raffinose fermentation (RAF) sorbitol fermentation (SOR), L-arabinose fermentation (LAR) and trehalose fermentation (TRE). The coding method is as follows.

| Coding Method | HEM+ — — | HYB– HIP– ADH+ | LAA– BGU+ BGA– | RIB+ RAF+ SOR+ | LAR– TRE+ LAC+ | Biological Code |
|---|---|---|---|---|---|---|
| 4-2-1 | 1 | 1 | 2 | 7 | 3 | 11273 |
| 1-2-4 | 1 | 4 | 2 | 7 | 6 | 14276 |

(11) To identify bacilli, the coding test items and the mediums in the paper-holes of biochemical properties-identifying papers are 15 kinds of tests and test mediums, which are those of are dihydrolase (ADH), urease (URE), citrate utilization (CIT) β-glucosidase (BGL), starch hydrolysis (AMD), L-arabinose fermentation (LAR), ribose fermentation (RIB), sorbitol fermentation (SOR), D-tagatose fermeatation (DTA), N-acetyl-glucosamine fermeatation (NAG), fructose fermentation (FRU), .mannose fermentation (MAS), galactose fermeatation (GAL), gentiobiose fermentation (GEN) and α-methyl-D-mannoside fermeatation (MDM). The coding method is as follows.

| Coding Method | ADH+ URE– CIT– | BGA+ AMD– LAR+ | RIB– SOR– DTA– | NAG– FRU+ MAS– | GAL– GEN– MDM+ | Biological Code |
|---|---|---|---|---|---|---|
| 4-2-1 | 4 | 5 | 0 | 2 | 1 | 45021 |
| 1-2-4 | 1 | 5 | 0 | 2 | 4 | 15024 |

(12) To identify lactobacilli, the coding test items and the mediums in the paper-holes of biochemical properties-identifying papers are 15 kinds of tests and test mediums, which are those of arbutine fermentation (ARB), ribose fermentation (RIB), N-acetyl-glucosamine fermentation (NAG), D-xylose fermentation (DXY) trehalose formentation (TRE), sorbitol fermentation (SOR), sucrose fermentation (SUC), lactose fermentation (LAC), cellobiose fermentation (CEL), melibiose fermentation (MEL), L arabinose fermeatation (LAR), rhamnose fermentation (RHA), D-tagatose fermentation (DTA), gluconate fermentation (GNT) and starch hydrolysis (AMD). The coding method is as follows.

| Coding Method | ARB– RIB+ NAG– | DXY– TRE+ SOR+ | SUC– LAC– CEL– | MEL+ LAR+ RHA– | DTA– GTA– AMD+ | Biological Code |
|---|---|---|---|---|---|---|
| 4-2-1 | 2 | 3 | 0 | 6 | 1 | 23061 |
| 1-2-4 | 2 | 6 | 0 | 3 | 4 | 26034 |

The aforementioned bacteria identification apparatus as a whole consists of image sampling unit, input unit, pro unit, storage unit, output unit and software system. The image sampling unit contains COD (Charger Coupled Devices) pickup camera and image sampling circuit. With the support of software, the CCD pickup camera transforms color-changing image which embodies bacteria biological properties into video signal being transfered into image sampling circuit. The image sampling circuit transforms the video signal from CCD pickup camera into digital signal to be processed by processing unit. The input unit consists of keyboard, keyboard circuit and their interface. The keyboard consists of 46 keys, which are 10 numeral keys, i. e. 0 to 9, 26 alphabet keys, i. e. A to Z, and 10 symbol keys, i. e ▲, ◄, ►, ▼, ←, →, +, −, CR, ES. The processing unit is 80286, 80386 or 80486 microprocessor and the relevant software. The storage unit uses the non-volatile semiconductor memory to store software and data. The non-volatile semiconductor memory is any one kind of programmable read-only memory, clearable programmable read-only memory or flash memory. The output unit ansists of color display and printer. The software consist of 4 system, which are system of identifeation, statistics, study and assistance. The identification system, which uses the present coding identification method as bacteria identification method, can identify 668 identification units of pathogen, conditional pathogen or opportunistic pathogen in 12 groups, which are common in clinic It can convert the inputted parameter of antibiotic sensitivity assay of the stain to be identified into sensitivity result, store the results of bacteria identification and antibiotic sensitivity assay and print the whole report list according to the request of the operator. In the course of bacteria identification, if there are several similar identification conclusions to a certain biological code or identification coding, the identification system can provide two kinds of identification pattern, which are direct identification, which draws the identification conclusion on genus and species of bacteria according to the identification value and standard likelihood value of the sin to be identified, and complementary identification, which identifies bacteria on the premise that the Identification system provides effective test items of complementary identification to the strain to be identified until the identification conclusion on genus and species of the strain is drawn. The study system in the systems software can study the test presentation of each identificaton unit in the identification system, the bacteria expression of the test presentation, the standard to explain the sensitivity extent of bacteria to antibiotics and the use method of the common used antibiotics. The assistance system in the system software can help the operator comprehensively understand every function of the identification apparatus, their use method and requests and can provide the operator color simulated image of test items of biological preporties of the strain to be identified and their combination selected by the operator to help him judge the test result correctly. The statistics system in the systems software can analyse the bacteria identification results, the assay results of antibiotic sensitivity and the data of patients et al stored by the user with 14 items of content to be statistically analysed including total detectable rate of various bacteria, detectable rate of various bacteria from different samples, detectable rate of various bacteria from different ages, detectable rate of various bacteria from different seasons, source distribution of the detectable bacteria, age distribution of the detectable bacteria, season distribution of the detectable bacteria, total drug-resistant rate of various bacteria, drug-resistant rate of the detectable bacteria from different samples, drog-resistant rate of the detectable bacteria from different ages, drug-resistant rate of the detectable bacteria from different seasons, source distribution of the drug-resistant strains age distribution of the drug-resistant strains, season distribution of the drug-resistant strains, and can output the analysis result by printing.

The aforementioned bacteria identification coding retrieval means is provided to determine the identification conclusion of genus and species of the strain to be identified and is obtained ed through precoding using numeral method according to the probable test presentation or biological coding of known bacteria in the combination of test items of the present oding identification method. It may be printed publication of Identification coding retrieval manual, computer coding retrieval system or computer analysis system. The bacteria identification coding retrieval mean is divided into 12 identification system according to the difference of biological groups of bacteria to be identified.

(1) identification coding retrieval system of parenteral gram-negative bacilli (2) identification retrieval system of enteric gram-negative bacilli (3) identification coding retrieval system of Enterobacteriaceae bacteria (4) identification coding retrieval system of anaerobic bacteria (5) identification coding retrieval system of neisseria/hemophilus (6) identification coding retrieval system of campylobacteria (7) identification coding retrieval system of yeast-like (8) identification coding retrieval system of corynebacteria (9) identification coding retrieval system of Micrococcaceae bacteria (10) identification coding retrieval system of streptoccaceae bacteria (11) identification coding retrieval system of bacilli (12) identification coding retrieval system of lactobacilli The coding test items and coding method of its biological code or identification code are as same as the aforementioned coding test items and coding method of identification system of bacteria in different groups. When the bacteria identification coding retrieval means is used to search the identification conclusion of genus and species of the strain to be identified, if there are several similar identification code, the bacteria identification coding retrieval system will provide effective complementary test items to further confirm the identification conclusion of tie strain to be identified Using the present coding identification method and identification apparatus, the number of identification unit and the identification rate of 12 groups of bacteria are as follows:

(1) In the identification system of parenteral gram-negative bacilli, there are 104 identification units and the identifiable rate is 94.9775%.

(2) Ii the identification system of enteric gram-negative bacilli, there are 108 identification units and the identifiable rate is 95.6386%.

(3) In the identification system of Enterobaeriaceae bacteria, there are 97 identification units and the identifiable rate is 97.6804%

(4) In the identification system of anaerobic bacteria, there are 80 identification units and the identifiable rate is 97.2151%

(5) In the identification system of neisseria/hemophilus, there are 30 identification units and the identifiable rate is 95.632%

9

(6) In the identification system of campylobacter, there are 18 identification units and the identifiable rate is 77.1241%

(7) In the identification system of yeast-like fungi, there are 80 identification units and the identifiable rate is 95.3917%

(8) In the identification system of corynebacteria, there are 33 identification units and the identifiable rate is 96.4015%

(9) III the identification system of Micrococcaceae bacteria, there are 85 identification units and the identifiable rate is 96.9747%

(10) In the identification system of Streptoccaceae bacteria, there are 47 identification units and the identifiable rate is 95.7446%

(11) In the identification system of bacilli, there are 24 identification units and the identifiable rate is 81.8840%

(12) In the identification system of lactobacilli, there are 29 identification units and the identifiable rate is 86.6995%

In the present invention, because the aforementioned combination of test items and test mediums are used in the coding identification method and biochemical properties-identifying papers, every test in the combination has identificaton value and the identificaton of every group of bacteria is efficient; because the number of test items in the combination and the sorts of test mediums in biochemical properties-identify papers are little and each test item has identification value, and there is less consumption and no waste.

Because the structure of every unit in the present identification apparatus is as a whole, it has simple structure and interface, small volume, convenient installation and adjustment, good qualities of maintenance and upkeep. The image sampling unit contains CCD pickup camera and image sampling circuit. With the support of software, the CCD pickup camera transforms color-changing image which embodies bacteria biological properties into video signal being transfered into image sampling circuit. The image sampling circuit transforms the video signal from CCD pickup camera into digital signal to be prosed by pro units. So it operates directly, quickly, sensitively, accurately and has simple structure. Because the keyboard of the input unit consists of 46 keys, which are 10 numeral keys, i.e-0 to 9, 26 alphabet keys, i.e. A to Z, and 10 symbol keys, i.e ▲, ◄, ►, ▼, ←, →, +, −, CR, ES, the operation of input is convenient. The storage medium of software system uses the non-volatile semiconductor memory, so it has simple structure and interface, small volume, high reliability and good stability and maintenance. The output unit consist of color display and printer, so the man-machine interface is effective and the needed data can be printed selectively according to the request of user.

Because the identification system in the software system of the present apparatus consists of 12 identification subsystems, its identification range is extensive and it can identify 668 identification units of pathogen, conditional pathogen or opportunistic pathogen in 12 groups which are comon in dinic. Because the identification system consists of two kinds of identification pattern, which are direct identification and complementary identification, in the course of bacteria identification, if there are several similar identification conclusions to a certain biological code or identification coding, it can make selection according to the need and draw the exact identification conclusion. Because there

10 is conversion system of assay parameter of antibiotic sensitivity of bacteria in the identification system, while the operator completes bacteria identification and assay of antibiotic sensitivity, he can input the assay parameter of antibiotic sensitivity into the system, which can automatically convert it into sensitivity extent and minimum inhibitory concentration range of the antibiotic to that bacterium when the system obtained the parameter. Because the identification system has functions of store and report, it can store the identification data and report the identification results according to the selection of the operator, and can provide the reader of the report the information of dinical pharmacology to help cure the bacteria in clinic when the results are reported. Because there is study system in the systems software, it can study the biological properties of every identification unit in the identification groups, the bacteria expression of test presentation, the standard to explain the assay results of antibiotic sensitivity and the use method of the common used antibiotics, and can conduct the contrast analysis of every two biological properties of every identification it. Because there is the assistance system in the systems software it can help the operator to understand, study and master every operation, function, selection and affect. Because there is statistics system in the software system, it can conduct every statistics and analysis to the stored identification data. Because color image of test results is allocated to study, assistance and identification system of the systems software, it can help the operator study or master the judgement standard and judgement method of various test results.

Because the aforementioned combination of test items is used in the present identification coding retrieval means, every test in the combination has identification value and the identification of every group of bacteria is efficient. Because the number of test items in the combination is little and every test item has identification value, there is less consumption and no waste because the, identificaton coding retrieval means consists of two kinds of identification pattern, which are direct identification and complementary identification, in the course of bacteria identification, if there ate several similar identification conclusions to a certain biological code, identifeation coding or a group of biological properties parameter, it can make selection according to the need and draw the correct identification conclusion.

The structure of the bacteria identification apparatus and the implementation examples, which are provided according to the present invention, are illustrated in detail as follows combining the additional figures of the directions.

DETAILED DESCRIPTION OF THE INVENTION

I. Embodiment of the bacteria identification apparatus (FIG. 1)

Figure 1:
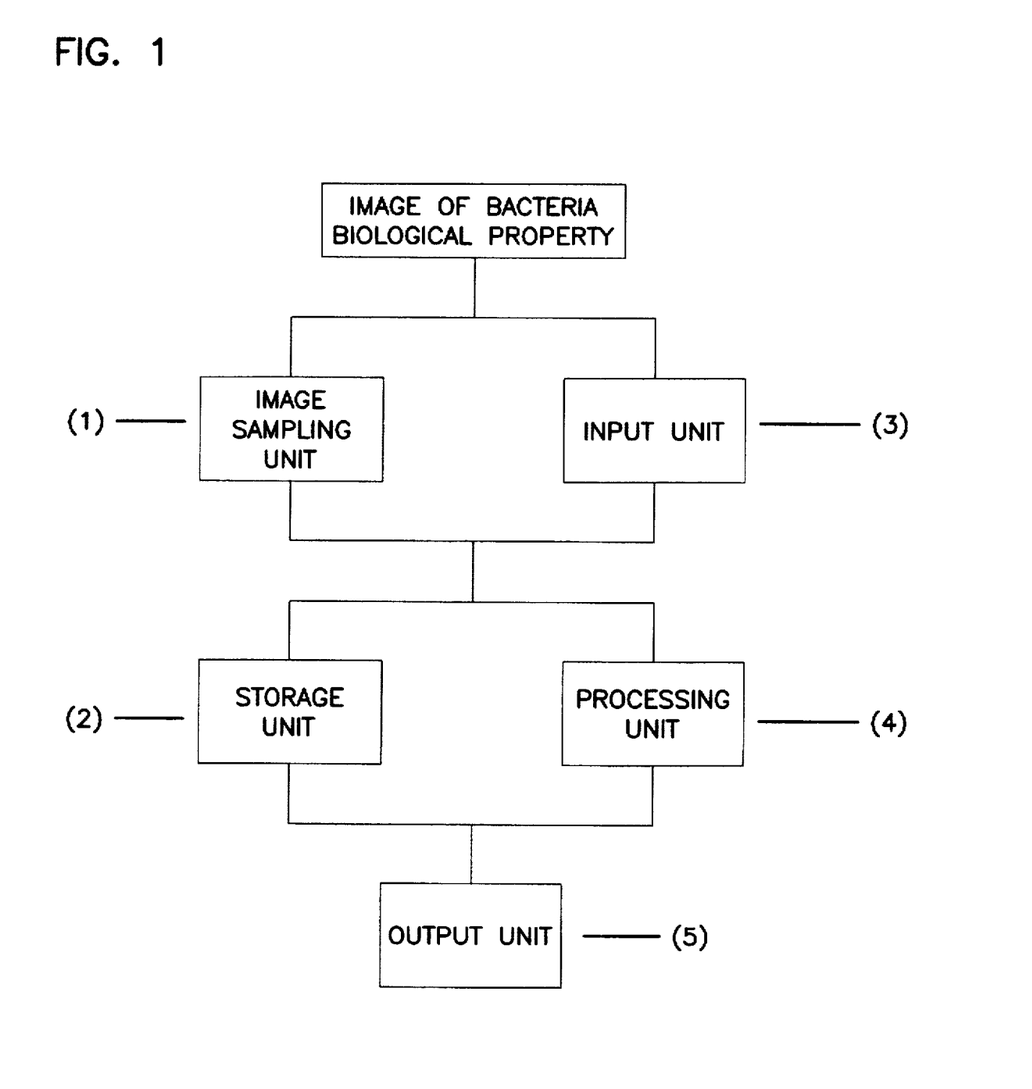
FIG. 1 is the sketch map of the structure of the bacteria identification apparatus.
Figure 2:
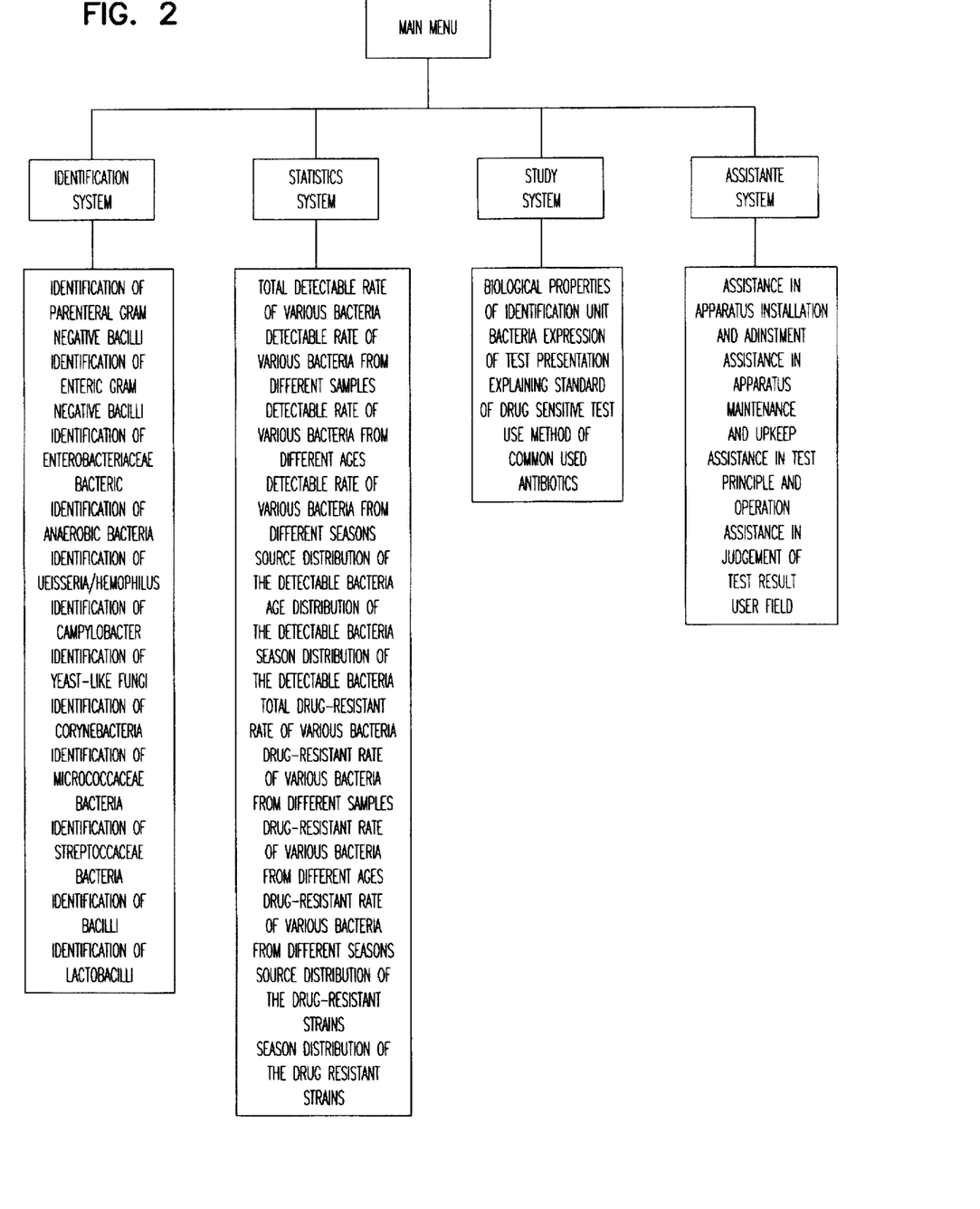
FIG. 2 is the maim mean diagram of systems software of the bacteria identification apparatus.

The bacteria identification apparatus as a whole is assembled by joining CCD pickup camera with connectors and interface of image sampling circuit of image sampling unit (1) keyboard (46 keys including 10 numeral keys, i. e. 0 to 9, 26 alphabet keys, i. e A to Z, and 10 symbol keys, i. e. ▲, ◄, ►, ▼, ←, →, +, −, CR, ES), keyboard circuit and its interface and connectors of input unit (3), microprocessor and its interface and connectors of prosing unit (4), memory and its interface and connectors of storage unit (2), color display and its circuit, interface and connectors and printer movement and its circuit, interface and connectors of output unit (5) each other, installing into the device box with power and power control switch, and writing software system into memory of storage unit (2) (See FIG. 1). The program block diagram of the software system is shown in FIG. 2.

II. Embodiment of Bacteria Identification Coding Retrieval Means.

(1) The bacteria identification coding retrieval manual is obtained by conducting precoding process to all biological codes of every system using numeral method according to the coding test items of bacteria identification and coding method of biological code, which are narrated in the directions, and making the results of precoding process into printed matter.

(2) The bacteria identification coding computer retrieval system is obtained by conducting precoding process to all biological codes of every system using numeral method according to the coding test items of bacteria identification and coding method of biological code, which are narrated in the directions, and storing the results of precoding process into floppy discs or hard disc of the computer.

(3) The bacteria identification coding compute analysis system is obtained by programming using numeral method according to the coding test items of bacteria identification and coding method of biological code, which are narrated in the directions.

III. Embodiment of Bacteria Biochemical Properties-Identifying Papers.

The a biochemical properties-identifying papers are made by preparing various test mediums in bacteria biochemical properties-identifying papers, adding them respectively into the holes of PVC material paper, which is shaped by injection using injection moulding machinary, and dried. The number of holes of PVC material paper in each kind of bacteria biochemical properties-identifying paper is as much as that of medium in the relevant bacteria biochemical properties-identifying paper, which is narrated in the directions. The sorts of medium are also as same as the narration in the directions.

IV. Embodiment of Bacteria Coding Identification Method

1. Embodiment of coding identification of parenteral gram-negative bacilli

| 2KG | 1 | CIT | 1 | NAG | 1 | SUC | 1 | GLU | 1 |
|---|---|---|---|---|---|---|---|---|---|
| 3HB | 2 | LPR | 2 | GLY | 2 | MEL | 2 | INO | 2 |
| OBU | 4 | HIS | 4 | MAL | 4 | FUC | 4 | MAN | 4 |

Coding identification test items:

| 1. 2KG | 2-keto-Gluconate assimilation |
| --- | --- |
| | 2-keto-gluconate assimilation test |
| 2. 3HB | 3-Hydroxy-Benzoate assimilation |
| | 3-hydroxy-benzoate assimilation test |
| 3. OBU | 3-Hydroxy-Butyrate assimilation |
| | 3-hydroxy-butyrate assimilation test |
| 4. CIT | CITrate assimilation |
| | citrate assimilation test |
| 5. LPR | L-PRoline assimilation |
| | l-proline assimilation test |
| 6. HIS | HIStidine assimilation |
| | histidine assimilation test |
| 7. NAG | N-Acetyl-d-Glucosamine assimilation |
| | N-acetyl-d-glucosamine assimilation test |
| 8. GLY | GLYcogen assimilation |
| | glycogen assimilation test |
| 9. MAL | MALtose assimilation |
| | maltose assimilation test |
| 10. SUC | SUCrose assimilation |
| | SUCrose assimilation test |
| 11. MEL | d-MELibiose assimilation |
| | D-melibiose assimilation test |
| 12. FUC | l-FUCose assimilation |
| | L-fucose assimilation test |
| 13. GLU | d-GLUcose assimilation |
| | D-glucose assimilation test |
| 14. INO | INOsitol assimilation |
| | Dinositol assimilation test |
| 15. MAN | MANnitol assimilation |
| | mannital assimilation test |

Complementary test items:

| 16. RHA | RHAmnose assimilation |
| --- | --- |
| | rhamnose assimilation test |
| 17. RIB | d-RIBose assimilation |
| | D-ribose assimilation test |
| 18. ITA | ITAconate assimilation |
| | itaconate assimilation test |
| 19. SUB | SUBerate assimilation |
| | suberate assimilation test |
| 20. MNT | MaloNaTe assimilation |
| | malonate assimilation test |
| 21. ACE | ACEtate assimilation |
| | acetate assimilation test |
| 22. LAT | dl-LAcTate assimilation |
| | DL-lactate assimilation test |
| 23. LAL | L-ALanine assimilation |
| | L-alanine assimilation test |
| 24. SAL | SALicin assimilation |
| | salicin assimilation test |
| 25. SOR | d-SORbitol assimilation |
| | D-sorbitol assimilation test |
| 26. LAR | L-ARabinose assimilation |
| | L-arabinose assimilation test |
| 27. PRO | PROpionate assimilation |
| | propionate assimilation test |
| 28. CAP | CAPrate assimilation |
| | caprate assimilation test |
| 29. VAL | VALeraTe assimilation |
| | valerate assimilation test |
| 30. 5KG | 5-keto-Gluconate assimilation |
| | 5-keto-gluconate assimilation test |
| 31. 4HB | 4-Hydroxy-Benzoate assimilation |
| | 4-hydroxy-benzoate assimilation test |
| 32. LSE | L-SErine assimilation |
| | L-serine assimilation test |

2. Embodiment of enteric gram-negative bacilli-coding identification method;

| OXI | 1 | LDC | 1 | IND | 1 | OFO | 1 | RHA | 1 |
|---|---|---|---|---|---|---|---|---|---|
| MCK | 2 | ODC | 2 | URE | 2 | MAN | 2 | AMY | 2 |
| MOT | 4 | ADH | 4 | CIT | 4 | SUC | 4 | SOR | 4 |

Coding identification test items:

| | | |
|---|---|---|
| 1* OXI | OXIdase | |
| | oxidase test | |
| 2* MCK | growth in MCK agar | |
| | growth in MCK agar test | |
| 3* MOT | MOTility | |
| | motility test | |
| 4* LDC | Lysine DeCarboxylase | |
| | lysine decarboxylase test | |
| 5. ODC | Ornithint Decarboxylase | |
| | ornithint decarboxylase test | |
| 6. ADH | Arginine DiHydrolase | |
| | arginine dihydrolase test | |
| 7. IND | INDole production | |
| | indole production test | |
| 8. URE | UREase | |
| | urease test | |
| 9. CIT | CITrate utilization | |
| | citrate utilization test | |
| 10. GLO | GLucose Oxidation | |
| | glucose oxidation test | |
| 11. MAN | MANnitol fermentation | |
| | mannitol fermentation test | |
| 12. SUC | SUCrose fermentation | |
| | sucrose fermentation test | |
| 13. RHA | RHAmnose fermentation | |
| | rhamnose fermentation test | |
| 14. AMY | AMYgdalin fermentation | |
| | amygdalin fermentation test | |
| 15. SOR | SORbitol fermentation | |
| | sorbitol fermentation test | |

Complementary test items:

| | | |
|---|---|---|
| 16. BGA | Beta-GAlactosidase | |
| | β-galactosidase test | |
| 17. NIT | reduction of NITrate | |
| | reduction of nitrate test | |
| 18. HIS | Hydrogen Sulfide production | |
| | hydrogen sulfide production test | |
| 19. TDA | Tryptophane DesAminase | |
| | tryptophane desaminase test | |
| 20. HYB | 3-Hydroxy-2-Butanone production | |
| | 3-hydroxy-2-butanone production test | |
| 21. GEL | GELatinase | |
| | gelatinase test | |
| 22. GLU | GLUcose Fermentation | |
| | glucose fermentation test | |
| 23. INO | INOsitol fermentation | |
| | inositol fermentation test | |
| 24. MEL | MELibiose fermentation | |
| | melibiose fermentation test | |
| 25. ARA | ARAbinose fermentation | |
| | arabinose fermentation test | |
| 26. NIG | NItrogen Gas production | |
| | nitrogen production test | |

-continued

| | | |
|---|---|---|
| 27 GLF | Glucose Fermentation | |
| | glucose fermentation test | |

3. Embodiment of Enterobacteriaceae bacteria-coding identification method

Coding test items of Interobacteriaceae bacteria

| LDC | 1 | URE | 1 | LAR | 1 | DUL | 1 |
|---|---|---|---|---|---|---|---|
| ODC | 2 | CEL | 2 | ADO | 2 | AMG | 2 |
| MAU | 4 | SOR | 4 | SUC | 4 | MAN | 4 |

Coding identification test items:

| | | |
|---|---|---|
| 1. LDC | Lysine DeCarboxylase | |
| | lysine decarboxylase test | |
| 2. ODC | Ornitine Decarboxylase | |
| | ornitine decarboxylase test | |
| 3. MAU | MAlonate Utilization | |
| | malonate utilization test | |
| 4. URE | UREase | |
| | urase test | |
| 5. CEL | CELlobiose fermentation | |
| | cellobiose fermentation test | |
| 6. SOR | D-SORbitol fermentation | |
| | D-sorbitol fermentation test | |
| 7. LAR | L-ARabinose fermentation | |
| | L-arabinose fermentation test | |
| 8. ADO | ADOnitol fermentation | |
| | adonitol fermentation test | |
| 9. SUC | SUCrose fermentation | |
| | sucrose fermentation test | |
| 10. DUL | DUlcitol fermentation | |
| | dulcitol fermentation test | |
| 11. AMG | Alpha-Methyl-D-Glucoside fermentation | |
| | α-methyl-D-glucoside fermentation test | |
| 12. MAN | D-MANnitol fermentation | |
| | D-mannitol fermentation test | |

Complementary test items:

| | | |
|---|---|---|
| 13. IND | INDole production | |
| | indole production test | |
| 14. MER | MERhyl red | |
| | merhyl red production test | |
| 15. HYB | 3-Hydroxy-2-Butanone production | |
| | 3-hydroxy-2-butanone production test | |
| 16. CIT | CITrate (Simons) | |
| | citrate utilization test | |
| 17. HYS | Hydrogen Sulfide (TSI) | |
| | hydrogen sulfide production test | |
| 18. PHE | PHEnylalanine deaminase | |
| | phenylalanine deaminase test | |
| 19. ADH | Arginine DiHydrolase | |
| | arginine dihydrolase test | |
| 20. MOT | MOTility | |
| | motility test | |
| 21. GEL | GELatin hydrolysis | |
| | gelatin hydrolysis test | |
| 22. KCN | growth in KCN | |
| | growth in KCN test | |
| 23. GLU | D-GLUcose, acid | |
| | D-glucose fermentation test with acid production | |

24. GLG  D-GLucose, Gas
         D-glucose fermentation test with gas production
25. LAC  LACtose fermentation
         lactose fermentation test
26. SAL  SALicin fermentation
         salicin fermentation test
27. INO  myo-INOsitol fermentation
         myo-inositol fermentation test
28. RAF  L-RAFfinose fermentation
         L-raffinose fermentation test
29. RHA  L-RHAmnose fermentation
         L-rhamnose fermentation test
30. MAL  MALtose fermentation
         maltose fermentation test
31. DXY  D-xylose fermentation
         D-xylose fermentation test
32. TRE  TREhalose fermentation
         trehalose fermentation test
33. ERY  ERYthitol fermentation
         erythitol fermentation test
34. ESC  ESCulin hydrolysis
         esculin hydrolysis test
35. MEL  MELibiose fermentation
         melibiose fermentation test
36. ART  D-ARabitol fermentation
         D-arabitol fermentation test
37. GLY  GLYcerol fermentation
         glycerol fermentation test
38. MUC  MUCate fermentation
         mucate fermentation test
39. TRA  TRAtrate, Jordon's
         tartrate utilization test
40. ACE  ACEtate utilization
         acetate utilization test
41. LIP  LIPase (corn oil)
         Lipase (corn oil) test
42. DNA  DNAse
         DNase test
43. NIT  reduction of NITrate
         reduction of nitrate test
44. OXI  OXIdase, kovuc's
         exidase test
45. BGA  Beta-GAlacotosidase
         β-galacotosidase test
46. YEL  YELlow pigment
         yellow pigment production test
47. MAS  D-MAnnoSe fermentation
         D-Mannose fermentation test 4. Embodiment of anaerobic bacteria-coding identification method:

Coding test items of anaerobic bacteria

[Figure: coding grid with cells GRS 1, SPO 2, AGL 1, AGA 2, AAR 4, BGL 1, BGA 2, BGU 4, LAA 1, PRA 2, ALP 4, IND 1, MAS 2, NAG 4]

Coding identification test items;

1 GRS  GRam Stain
       gram stain test
2 SPO  SPOrulation
       sporulation test
3. AGL  Alpha-GLUcosidase
        α-glucosidase test
4. AGA  Alpha-GAlactosidase
        α-galactosidase test
5 AAR   Alpha-ARabinosidase
        α-arabinasidase test
6. BGL  Beta-Glucosidase
        β-glucosidase test
7. BGA  Beta-GAlactosidase
        β-galactosidase test
8. BGU  Beta-GlucUronidase
        β-glucuronidase test
9. LAA  Leucine ArylAmidase
        leucine aryamidase test
10. PRA PRoline Arylamidase
        proline arylamidase test
11. ALP ALKaline Phosphatase
        alkaline phosphatase test
12. IND INDole production
        indole production test
13. MAS MAnnose fermentation
        mannose fermentation test
14. NAG N-Acetyl-β-d-Glucosaminidase
        N-acetyl-β-D-Glucosaminidase test
15. URE UREase
        urase test
16. ADH Arginine DiHydrolase
        arginine dihydrolase test
17. BGP Beta-Galactosidase-6-phosphate
        β-galactosidose-6-phosphate test
18. RAF RAFfinose fermentation
        raffinose fermentation test
19. NIT reduction of NITrate
        reduction of nitrate test
20. AAA Arginine ArylAmidase
        arginine arylamidase test
21. LGA Leucyl Glycine Arylamidase
        leucyl glycine arylamidase test
22. PAA Phenylalanine Arylamidase
        phyenylalanine aryamidase test
23. PYA Pyroglutamic ac. Arylamidase
        pyroglutamic acid arylamidase test
24. TAA Tyrosine Arylamidase
        tyrosine anglamidase test
25. ALA Alanine Arylamidase
        alanine arylamidase test
26. GAA Glycine ArylAmidase
        glycine arylamidase test
27. GAD Glutamic Ac. Decarboxylase
        glutamic acid decarboxy lase test
28. AFU Alpha-FUcosidase
        α-fucosidase test
29. HAA Histidine ArylAmidase
        histidine arylamidase test
30. GGA GLutamyl GLutamic ac. Arylmidase
        glutamyl glutamic acid arylmidase test
31. SAA Serine ArylAmidase
        serine arylamidase test
32. MOR MORphology
        morphology test

5. Embodiment of neisseria/hemophilus-coding identification method:

Coding test items of neisserial hemophilus

| CAT | 1 | MTM | 1 | BGA | 1 | GGT | 1 |
|---|---|---|---|---|---|---|---|
| | | GLU | 2 | OPS | 2 | PRO | 2 |
| | | MLT | 4 | GLY | 4 | RES | 4 |

Coding test items

| | | |
|---|---|---|
| 1* | CAT | CATalase |
| | | catalase test |
| 2. | MTM | Martin-Thayer Medium |
| | | growth in Martin-Thayer medium test |
| 3. | GLU | GLUcose |
| | | glucose fermentation test |
| 4. | MLT | MaLTose fermentation |
| | | maltose fermentation test |
| 5. | BGL | Beta-GLucosidase |
| | | β-glucosidase test |
| 6. | OPS | PhenylphoSphonate |
| | | phenylphosphonate test |
| 7. | GLY | GLYcine-p-nitroanilide |
| | | glycine-p-nitroanilide test |
| 8. | GGT | Gamma-GLutarmyl-p-niTroanilide |
| | | γ-glutarmyl-p-nitroamilide test |
| 9. | PRO | PROline-p-nitroaniclide |
| | | proline-p-nitroanilide test |
| 10. | RES | RESazurin |
| | | resazurin test |

Complimentary test items

| | | |
|---|---|---|
| 11. | ALA | ALanine-penitroanilide |
| | | alanine-penitroanilide test |
| 12. | LYS | LYSine-p-nitroanilide |
| | | lysine-p-nitroanilide test |
| 13. | PNC | P-Nitrophenyl-phosphonyl-cholinr |
| | | p-nitrophenyl-phosphonyl-cholinr test |
| 14. | SUC | SUCrose fermentation |
| | | sucrose fermentation test |
| 15. | TTZ | TriphenylTetraZolium |
| | | triphenyltetrazolium test |
| 16. | ORN | ORNithine decarboxylase |
| | | ornithine decarboxylase test |
| 17. | URE | UREase |
| | | urase test |
| 18. | PEN | PENicillin G Sensibility |
| | | penicillin g sensibility test |

6. Embodiment of campylobacter-coding identification method

Test items of campybacter

| CAT | 1 | SUC | 1 | HYS | 1 |
|---|---|---|---|---|---|
| NIT | 2 | ACE | 2 | GGT | 2 |
| URE | 4 | HIP | 4 | ALP | 4 |

Coding test items:

| | | |
|---|---|---|
| 1. | CAT | CATalase |
| | | catalase test |
| 2. | NIT | reduction of NITrate |
| | | reduction of nitrate test |
| 3. | URE | UREase |
| | | urease test |
| 4. | SUT | SUccinaTe assimilation |
| | | succinate assimilation test |
| 5. | ACE | ACEtate assimilation |
| | | acetate assimilation test |
| 6. | HIP | HIPpurate hydrolysis |
| | | hippurate hydrolysis test |
| 7. | HYS | HYdrogen Sulfide production |
| | | hydrogen sulfide production test |
| 8. | GGT | Gama-GLutamyl Transferase |
| | | γ-glutamyl transferase test |
| 9. | ALP | ALPaline phosphatase |
| | | alkaline phosphatase test |

Complementary test items:

| | | |
|---|---|---|
| 10. | EST | ESTerase |
| | | esterase test |
| 11. | TTC | reduction chlorure Triphenyl Transferase |
| | | reduction chlorure triphenyl transferase test |
| 12. | PYR | PYRrolidonyl arylamidase |
| | | pyrrolidonyl arylamidase test |
| 13. | ARY | L-ARYinine arylamidase |
| | | L-aryinine arylamidase test |
| 14. | ASP | L-ASPartate arylamidase |
| | | L-aspartate arylamidase test |
| 15. | GLU | GLUcose assimilation |
| | | glucose assimilation test |
| 16. | NAL | NALidixigue sensibility |
| | | nalidixique sensibility test |
| 17. | CFZ | CeFazoline sensibility |
| | | cefazoline sensibility test |
| 18. | PRO | PROpinate assimilation |
| | | propinate assimilation test |
| 19. | MLT | MaLaTe assimilation |
| | | malate assimilation test |
| 20. | CIT | CITrate assimilation |
| | | citrate assimilation test |
| 21. | ERS | ERythomycine Sensibility |
| | | erythomycine sensibility test |

7. Embodiment of yeast-like fungi-coding identification method:

Coding test items of yeast-like fungi

| 2 | 1 | | M | 1 | | L | 1 | | C | 1 | | M | 1 |
|---|---|---|---|---|---|---|---|---|---|---|---|---|---|
| K | | | A | | | A | | | E | | | E | |
| G | | | N | | | R | | | L | | | L | |
| A | 2 | | I | 2 | | G | 2 | | L | 2 | | T | 2 |
| C | | | N | | | A | | | A | | | R | |
| T | | | O | | | L | | | C | | | E | |
| E | 4 | | N | 4 | | R | 4 | | M | 4 | | E | 4 |
| R | | | A | | | A | | | A | | | S | |
| Y | | | G | | | F | | | L | | | C | |

Coding test items:

1. 2KG  2-keto-Gluconate assimilation
    2-keto-gluconate assimilation test
2. ACT  ACTidone assimilation
    actidone assimilation test
3. ERY  ERYthritol assimilation
    erythritol assimilation test
4. MAN  MANnitol assimilation
    mannitol assimilation test
5. INO  INOsitol assimilation
    inositol assimilation test
6. NAG  N-Acetnyl-d-Glucosamine assimilation
    N-acetnyl-D-glucosamine assimilation test
7. LAR  L-ARabinose assimilation
    L-arabinese assimilation test
8. GAL  GALactose assimilation
    galactose assimilation test
9. RAF  RAFfinose assimilation
    roffinose assimilation test
10. CEL  CELlobose assimilation
    cellobose assimilation test
11. LAC  LACtose assimilation
    lactose assimilation test
12. MAL  MALtose assimilation
    maltose assimilation test
13. MEL  MELibiose assimilation
    melibiose assimilation test
14. TRE  TREhalose assimilation
    trehalose assimilation test
15. ESC  ESCulin assimilation
    esculin assimilation test Complementary test items 16. SUC  SUCrose assimilation
    sucrose assimilation test
17. LST  DL-LAcTate assimilation
    DL-lactate assimilation test
18. MDG  α-Methyl-D-Glucoside assimilation
    α-methyl-D-glucoside assimilation test
19. SOR  SORbitol assimilation
    sorbitol assimilation test
20. DXY  D-xylose assimilation
    D-xylose assimilation test
21. RIB  RIBose assimilation
    ribose assimilation test
22. GLY  GLYcerl assimilation
    glycerl assimilation test
23. RHA  RHAmnose assimilation
    rhamnose assimilation test
24. PLF  PaLatinosE assimilation
    palatinose assimilation test
25. MLZ  MeLeZitose assimilation
    melezitose assimilation test
26. GRT  GLucuRonaTe assimilation
    glucuronate assimilation test
27. GNT  GlucoNaTe assimilation
    gluconate assimilation test
28. LVT  LeVullinaTe assimilation
    levullinate assimilation test
29. GLU  GLUcose assimilation
    glucose assimilation test
30. SBE  SorBosE assimilation
    sorbose assimilation test
31. GLN  GLucosamiNe assimilation
    glucosamine assimilation test

8. Embodiment of congnebacteria-coding identification method

Coding test items of corynebacteria

| N | 1 | | M | 1 | | L | 1 |
|---|---|---|---|---|---|---|---|
| I | | | A | | | A | |
| T | | | L | | | C | |
| U | 2 | | S | 2 | | A | 2 |
| R | | | U | | | G | |
| E | | | C | | | L | |
| E | 4 | | R | 4 | | B | 4 |
| S | | | I | | | G | |
| C | | | B | | | A | |

Coding test items

1. NIT  reduction of NITrate
    reduction of intrate test
2. URE  UREase
    urease test
3. ESC  ESCulin
    esculin test
4. MAL  l-MALtose fermentation
    L-maltose fermentation test
5. SUC  SUCrose fermentation
    sucrose fermentation test
6. RIB  RIBose fermentation
    ribose fermentation test
7. LAC  LACtose fermentation
    lactose fermentation test
8. AGL  Alpha-GLucosidase
    α-glucosidase test
9. BGA  Beta-GAlactosidase
    β-galactosidase test
10. PYZ  PYraZinamidase
    pyrazinamidase test
11. PYR  PYRrolidonyl arylamidse
    pyrrolidonyl arylamidse test
12. ALP  ALkaline phosphate
    alkaline phosphate test
13. BGU  Beta-GlucUronidase
    β-glucuronidase test
14. NAG  N-Acetyl-β-Glucosaminidase
    N-acetyl-β-D-glucosaminidase test
15. GEL  GELatine hydrolysis
    gelatine hydrolysis test
16. GLF  GLucose Fermentation
    glucose fermentation test
17. XYL  XYLose fermentation
    xylose fermentation test

| 18. MAN | MANitol fermentation |
| | manitol fermentation test |
| 19. GLY | GLYcogen fermentation |
| | glycogen fermentation test |
| 20. CAT | CATalase |
| | catalase Test |

9. Embodiment of Micrococcaceae bacteria-coding identification method
Coding test items of micrococcaceae bacteria

| U | 1 | | A | 1 | | B | 1 | | S | 1 |
| R | | | D | | | G | | | U | |
| E | | | H | | | A | | | C | |
| N | 2 | | O | 2 | | B | 2 | | M | 2 |
| I | | | D | | | G | | | A | |
| T | | | G | | | U | | | N | |
| V | 4 | | A | 4 | | G | 4 | | T | 4 |
| | | | L | | | L | | | R | |
| P | | | P | | | U | | | E | |

Coding test items:

| 1. URE | UREase |
| | urease test |
| 2. NIT | reduction of NITrate |
| | reduction of nitrate test |
| 3. V—P | acetion production |
| | acetion production test |
| 4. ADH | Arginine DiHydrolase |
| | arginine dihydrolase test |
| 5. ODC | Ornithine DeCarboxylase |
| | ornithine decarboxylase test |
| 6. ALP | ALkaline phosphatase |
| | alkaline phosphatase test |
| 7. BGA | Beta-GAlactosidase |
| | β-galactosidase test |
| 8. BGU | Beta-GlucUronidase |
| | β-glucuronidase test |
| 9. GLF | GLucose Fermentation |
| | glucose fermentation test |
| 10. SUC | SUCrose fermentation |
| | sucrose fermentation test |
| 11. MAN | MANnitol fermentation |
| | mannitol fermentation test |
| 12. TRE | TREhalose fermentation |
| | trehalose fermentation test |

Complementary test items:

| 13. ESC | ESCulin hydrolysis |
| | esculine hydrolysis test |
| 14. FRU | FRUctose fermentation |
| | fructose fermentation test |
| 15. MAS | MAnnoSe fermentation |
| | mannose fermentation test |
| 16. MAL | MALtose fermentation |
| | maltose fermentation test |
| 17. LAC | LACtose fermentation |
| | lactose fermentation test |
| 18. RAF | RAFfinose fermentation |
| | raffinose fermentation test |
| 19. ARG | ARGinine argiamidase |
| | arginine argiamidase test |
| 20. PYR | PYRrolidonyl arylamidase |
| | pyrrolidonyl arylamidase test |
| 21. NOV | NOVobocin (Resistance) |
| | novobiocin test |
| 22. NAG | N-Acetyl-GLUcosamine Fermentation |
| | N-acetyl-glucosamine fermentation test |
| 23. TUR | TURranose fermentation |
| | turanose fermentation test |
| 24. ARA | ARAbinose fermentation |
| | arobinose fermentation test |
| 25. RIB | RIBose fermentation |
| | ribose fermentation test |
| 26. CEL | CELlubiose fermentation |
| | cellubiose fermentation test |

10. Embodiment of Streptoccaceae bacteria-coding identification method:
Coding test items of Streptoccaceae bacteria

| V | 1 | | L | 1 | | R | 1 | | L | 1 |
| | | | A | | | I | | | A | |
| P | | | A | | | B | | | R | |
| H | 1 | | H | 2 | | B | 2 | | R | 2 | | T | 2 |
| E | | | I | | | G | | | A | | | R | |
| M | | | P | | | U | | | F | | | E | |
| A | 4 | | B | 4 | | S | 4 | | L | 4 |
| D | | | G | | | O | | | A | |
| H | | | A | | | R | | | C | |

Coding test items:

| 1* HEM | HEMolysis |
| | hemolysis test |
| 2. V—P | aceton production |
| | aceton production test |
| 3. HIP | HIPpurate hydrolysis |
| | hippurate hydrolysis test |
| 4. ADH | Arginine DiHydrolase |
| | arginine dihydrolase test |
| 5. LAA | α-Leucine ArylAmidase |
| | α-leucine arylamidase test |
| 6. BGU | Beta-GLucUronidase |
| | β-glucuronidase test |
| 7. BGA | Beta-GAlactosidase |
| | β-galactosidase test |
| 8. RIB | RIBose fermentation |
| | ribose fermentation test |
| 9. RAF | RAFfinose fermentation |
| | raffinose fermentation test |
| 10. SOR | SORbitol fermentation |
| | sorbitol fermentation test |
| 11. LAR | L-ARabinose fermentation |
| | L-arabinose fermentation test |
| 12. TRE | TREhalose fermentation |
| | trehalose fermentation test |
| 13. LAC | LACtose fermentation |
| | lactose fermentation test |

Complementary test items:

| 14. ESC | ESCulin hydrolysis |
| | esculin hydrolysis test |
| 15. PYR | Pyrrolidonyl arylamidase |
| | pyrrolidonyl arylamidase test |

| 16. AGA | Alpha-GAlactosidase |
| | α-GAlactosidase test |
| 17. ALP | ALkalische phosphatase |
| | alkalische phosphatase test |
| 18. MAN | MANnitol fermentation |
| | mannitol fermentation test |
| 19. INU | INUlin fermentation |
| | inulin fermentation test |
| 20. AMD | Starch |
| | starch hydrolysis test |
| 21. GLY | GLYcogen fermentation |
| | glycogen fermentation test |

11. Embodiment of bacilli-coding identification method:
Coding test items of bacilli

| A | 1 | | O | 1 | | R | 1 | | N | 1 | | G | 1 |
|---|---|---|---|---|---|---|---|---|---|---|---|---|---|
| D | | | N | | | I | | | A | | | A | |
| H | | | P | | | B | | | G | | | L | |
| U | 2 | | A | 2 | | S | 2 | | F | 2 | | G | 2 |
| R | | | M | | | O | | | R | | | E | |
| E | | | D | | | R | | | U | | | N | |
| C | 4 | | L | 4 | | D | 3 | | M | 4 | | M | 4 |
| I | | | A | | | T | | | A | | | D | |
| T | | | R | | | A | | | S | | | M | |

Coding test items:

| 1. ADH | Arginine DIHydrolase |
| | arginine dihydrolase test |
| 2. URE | Urase |
| | urase test |
| 3. CIT | CITrate utilization |
| | citrate utilization test |
| 4. ONP | Ortho-Nitro-phenyl-Galactoside |
| | ortho-nitro-phenyl-galactoside test |
| 5. AMD | Starch |
| | starch hydrolysis test |
| 6. LAR | L-ARabircose fermentation |
| | L-arabircose fermentation test |
| 7. RIB | RIBose fermentation |
| | ribose fermentation test |
| 8. SOR | SORbitol fermentation |
| | sorbitol fermentation test |
| 9. DTA | D-TAgatose fermentation |
| | D-tagatose fermentation test |
| 10. NAG | N-Acetyl-Glucoseamine fermentation |
| | N-acetyl-glucoseamine fermentation test |
| 11. FRU | FRUctose fermentation |
| | fructose fermentation test |
| 12. MAS | MAnnoSe fermentation |
| | mannose fermentation test |
| 13. GAL | GALactose fermentation |
| | galactose fermentation test |
| 14. GEN | GENtiobiose fermentation |
| | gentiobiose fermentation test |
| 15. MDM | α-Methyl-D-Mannoside fermentation |
| | α-methyl-D-mannoside fermentation test |

Complementary test items:

| 16. GLY | GLYcerol fermentation |
| | glycerol fermentation test |
| 17. ERY | ERYthritol fermentation |
| | erythritol fermentation test |
| 18. DAR | D-ARabinose fermentation |
| | D-arabinose fermentation test |
| 19. DXY | D-XYlose fermentation |
| | D-xylose fermentation test |
| 20. LXY | L-XYlose fermentation |
| | L-xylose fermentation test |
| 21. ADO | ADOnitol fermentation |
| | adonitol fermentation test |
| 22. MDX | β-Methyl-D-Xyloside fermentation |
| | β-methyl-D-xyloside fermentation test |
| 23. GLF | GLucose Fermentation |
| | glucose fermentation test |
| 24. SOS | SOrboSe fermentation |
| | sorbose fermentation test |
| 25. RHA | RHAmnose fermentation |
| | rhamnose fermentation test |
| 26. DUL | DUlcitol fermentation |
| | dulcitol fermentation test |
| 27. INO | INOsitol fermentation |
| | inositol fermentation test |
| 28. MAN | MANnitol fermentation |
| | mannitol fermentation test |
| 29. MDM | Methyl-D-Mannoside fermentation |
| | α-methyl-D-mannoside fermentation test |
| 30. MDG | α-Methyl-D-Glucoside fermentation |
| | α-methyl-D-glucoside fermentation test |
| 31. AMY | AMYgdaline fermentation |
| | amygdaline fermentation test |
| 32. ARB | ARButine fermentation |
| | arbutine fermentation test |
| 33. ESC | ESCuline |
| | esculine hydrolysis test |
| 34. SAL | SAlicine fermentation |
| | solicine fermentation test |
| 35. TCEL | CELlubiose fermentation |
| | cellubiose fermentation test |
| 36. MAL | MALtose fermentation |
| | maltose fermentation test |
| 37. LAC | LACtose fermentation |
| | lactose fermentation test |
| 38. MEL | MELibiose fermentation |
| | melibiose fermentation test |
| 39. SAC | SACvharose fermentation |
| | sacvharose fermentation test |
| 40. TRE | TREhalone fermentation |
| | trehalone fermentation test |
| 41. INU | INUilne fermentation |
| | inuline fermentation test |
| 42. MLZ | MeLeZitose fermentation |
| | melezitose fermentation test |
| 43. RAF | RAFfinose fermentation |
| | raffinose fermentation test |
| 44. GLG | GLycoGen fermentation |
| | glycogen fermentation test |
| 45. XLT | XyLiTol fermentation |
| | xylitol fermentation test |
| 46. DLY | D-LYxose fermentation |
| | D-lyxose fermentation test |
| 47. DFU | D-FUcose fermentation |
| | D-fucose fermentation test |
| 48. LFU | L-FUcose fermentation |
| | L-fucose fermentation test |
| 49. DAR | D-ARabiol fermentation |
| | D-arabitol fermentation test |
| 50. LAR | L-ARabiol fermentation |
| | L-arabitol fermentation test |
| 51. GNT | GlucoNaTe |
| | guconate test |
| 52. 2KG | 2-keto-Gluconate |
| | 2-keto-gluconate test |
| 53. 5KG | 5-keto-Gluconate |
| | 5-keto-gluconate test |
| 54. LDC | Lysine DeCarboxylase |
| | lysine decarboxylase test |
| 55. ODC | Ornithine DeCarboxylase |
| | ornithine decarboxylase test |
| 56. HYS | Hydrogen sulfide production |
| | hydrogen sulfide production test |

| | |
|---|---|
| 57. TDA | Tyrptophane DesAminase |
| | tyrptophane desaminase test |
| 58. IND | INDole production |
| | indole production test |
| 59. V—P | acetion production |
| | acetion production test |
| 60. GEL | GELatinase |
| | gelatinase test |
| 61. NIT | reduction of NITrates |
| | reduction of nitrates test |

12. Embodiment of lactobacilli-coding identification method:
Coding test items of lactobacilli

| A R B | 1 | D X Y | 1 | S A C | 1 | M E L | 1 | D T A | 1 |
|---|---|---|---|---|---|---|---|---|---|
| R I B | 2 | T R E | 2 | L A C | 2 | L A R | 2 | G N T | 2 |
| N A G | 4 | S O R | 4 | C E L | 4 | R H A | 4 | A M D | 4 |

Coding test items:

| | |
|---|---|
| 1. ARB | ARButine fermentation |
| | arbutine fermentation test |
| 2. RIB | RIBose fermentation |
| | ribose fermentation test |
| 3. NAG | N-Acetyl-Glucosamine fermentation |
| | N-acetyl-glucosamine fermentation test |
| 4. DXY | D-XYlose fermentation |
| | D-xylose fermentation test |
| 5. TRE | TREhalose fermentation |
| | trehalose fermentation test |
| 6. SOR | SORbitol fermentation |
| | sorbitol fermentation test |
| 7. SUC | SUCrose fermentation |
| | sucrose fermentation test |
| 8. LAC | LACtose fermentation |
| | lactose fermentation test |
| 9. CEL | CELlobiose fermentation |
| | cellobiose fermentation test |
| 10. MBL | MELibiese fermentation |
| | melibose fermentation test |
| 11. LAR | L-ARAbinose fermentation |
| | L-arabinose fermentation test |
| 12. RHA | RHAmnose fermentation |
| | rhamnose fermentation test |
| 13. DTA | D-TAgatose fermentation |
| | D-tagatose fermentation test |
| 14. GNT | GlucoNaTe fermentation |
| | gluconate fermentation test |
| 15. AMD | starch fermentation |
| | starch fermentation test |

Complementary test item:

| | |
|---|---|
| 16. GLY | GLYcerol fermentation |
| | glycerol fermentation test |
| 17. ERY | ERYthritol fermentation |
| | erythritol fermentation test |
| 18. ARA | D-ARAbinose fermentation |
| | D-arabinose fermentation test |
| 19. XYL | L-XYLose fermentation |
| | L-xylose fermentation test |
| 20. ADO | ADOnitol fermentation |
| | adonitol fermentation test |
| 21. MDX | β-Methyl-D-Xyloside fermentation |
| | β-methyl-D-xyloside fermentation test |
| 22. GAL | GALactose fermentation |
| | galactose fermentation test |
| 23. GLU | GLUcose fermentation |
| | glucose fermentation test |
| 24. FRU | FRUctose fermentation |
| | fructose fermentation test |
| 25. MNE | MaNnosE fermentation |
| | mannose fermentation test |
| 26. SOS | SorboSe fermentation |
| | sorbose fermentation test |
| 27. DUL | DULcitol fermentation |
| | dulcitol fermentation test |
| 28. INO | INOnitol fermentation |
| | inonitol fermentation test |
| 29. MAN | MANnitol fermentation |
| | mannitol fermentation test |
| 30. MDM | α-Methyl-D-Mannoside fermentation |
| | α-methyl-D-mannoside fermentation test |
| 31. MDG | α-Methyl-D-GLUcoside fermentation |
| | α-methyl-D-glucoside fermentation test |
| 32. AMY | AMYgdaline fermentation |
| | amygdaline fermentation test |
| 33. ESC | ESCuline |
| | esculine hydrolysis test |
| 34. SAL | SALicin fermentation |
| | salicin fermentation test |
| 35. MAL | MALtose fermentation |
| | maltose fermentation test |
| 36. INU | INUline fermentation |
| | inuline fermentation test |
| 37. MLZ | MeLeZitose fermentation |
| | melezitose fermentation test |
| 38. RAF | RAFfinose fermentation |
| | raffinose fermentation test |
| 39. GLG | GLycoGene fermentation |
| | glycogene fermentation test |
| 40. XLT | XyLiTol fermentation |
| | xylitol fermentation test |
| 41. GEN | GENtiobiose fermentation |
| | gentiobiose fermentation test |
| 42. TUR | D-TURanose fermentation |
| | D-turanose fermentation test |
| 43. LYX | D-LYXose fermentation |
| | D-lyxose fermentation test |
| 44. DFU | D-FUcose fermentation |
| | D-fucose fermentation test |
| 45. LFU | L-FUcose fermentation |
| | L-fucose fermentation test |
| 46. DAR | DARabitol fermentation |
| | D-arabitol fermentation test |
| 47. LAR | L-ARabitol fermentation |
| | L-arabitol fermentation test |
| 48. 2KG | 2-keto-GLuconate |
| | 2-keto-gluconate test |
| 49. 5KG | 5-keto-GLuconate |
| | 5-keto-gluconate test |

We claim:

1. A bacteria identification method which uses coding test items and biochemical property, identifying papers that detect biological properties of bacterial strains characterized in that the coding test items in the bacteria-coding identification system are one of the following 12 kinds of combination;

(1) the coding test items of identifying parenteral gram-negative bacilli are 15 tests of 2-keto-gluconate (2 KG), 3-hydroxy-benzoate (3 HB), 3-hydroxy-butyrate (OBU), citrate (CIT), L-proline (LPR), histosc (HIS), N-acetyl-D-glucosamine (NAG), glycogen (GLY), maltose (MAL), sucrose (SUC), D-melibiose (MEL), L-fucose (FUC), D-glucose (GLU), inositol (INO), and manitol (MAN);

(2) the coding test items of identifying enteric gram-negative bacilli are 15 tests of oxidase (OXI), growth in MCK agar (MCK), motility (MOT), lysine decarboxylase (LDC), ornithint decarboxylase (ODC), arginine dihydrolase (ADH), indole production (IND), urease (URE), citrate utilization (CIT), glucose oxidation (GLO), mannitol fermentation (MAN), sucrose fermentation (SUC), rhamnose fermentation (RHA), amygdalin fermentation (AMY), and sorbitol fermentation (SOR);

(3) the coding test items of identifying Enterobacteriaceae bacteria are 12 tests of lysine decarboxylase (LDC), ornitine decarboxylase (ODC), malonate utilization (MAU), urease (URE), cellobiose fermentation (CEL), D-sorbitol fermentation (SOR), L-arabinose fermentation (LAE), adoonitol fermentation (ADO), surcose fermentation (SUC), dulcitol fermentation (DUL), α-methyl-D-glucose fermentation (AMG) and D-mannitol fermentation (MAN);

(4) the coding test items of identifying anerobic bacteria are 14 tests of gram stain (GRS), sporulation (SPO), α-arabirosidase (AAR), β-glucosidase (BGL), β-galactosidase (BGA), β-glucuronidase (BGU), laucine arylamidaes (LAA), proline arylamidase (PRA), alakaline phosphatase (ALP), indole production (IND), mannose fermentation (MAS), and β-N-acetyl-glycosaminidase (NAG);

(5) the coding test items of identifying neisserial hemophilus are 9 tests of catalose (CAT), growth in Martin-Thayer medium (MTM), lucose fermentation (GLU), maltose fermentation (MLT), β-glucosidase (BGL), phenylphosphonate (OPS), glycine anglamidase (GLY), γ-glutamyl arylamidase (GGT), proline arylamidase (PRO) and reduction of resazurin (RES);

(6) the coding test items of identifying compylbacter are 9 tests of catalase (CAT), reduction of nitrate (NIT), urease (URE), succinate assimilation (SUT), acetate assimilation (ACE), hippurate hydrolysis (HIP), hydrogen sulfide production (HYS), γ-glycotamyl transferase (GGT) and alkaline phosphatose (ALP);

(7) the coding test items of identifying yeast-like fungi are 15 tests of 2-keto-gluconate (2 KG), actidine (ACT), erythritol (ERY), mannitol (MAN), inositol (INO), N-acetyl-glucosamine (NAG), L-arabinose (LAR), galatose (GAL), raffinose (RAF), cellobose (CEL), lactose (LAC), maltose (MAL), melibiose (MEL), trehalsoe (TRE) and esculin (ESC);

(8) the coding test items of identifying corynebacteria are 9 tests of reduction of nitrate (NIT), urease (URE), esculin hydrolysis (ESC), L-maltose fermentation (MAL), sucrose fermentation (SUC), ribose fermentation (RIB), lactose fermentation (LAC), α-glucosidase (AGL) and β-galactosidase (BGA);

(9) the coding test items of identifying micrococcaceae bacteria are 12 tests of urease (URE), reduction of nitrte (NIT), 3-hydroxyl-butanone production (HYB), arginine dihydrolase (ADH), ornithine decarboxylase (ODC), alkaline phosphatase (ALP), β-galactosidase (BGA), β-glucuronidase (BGU), glucose fermentation (GLF), sucrose fermentation (SUC), mannitol fermentation (MAN) and trehalose fermentation;

(10) the coding test items of identifying Streptoccaceae bacteria are 13 tests of hemdysis (HEM), 3-hydroxy-butanone production (HYB), hippurate hydrolysis (HIP), arginine dihydrolase (ADH), L-leucine arylamidase (LAA), β-glucuronidase (BGU), β-galactosidase (BGA), ribose fermentation (RIB), raffinose fermentation (RAF), sorbitol fermentation (SOR), L-arabinose fermentation (LAR) and trehalose fermentation (TRE);

(11) the coding test items of identifying bacilli are: 15 tests of arginine dihydrolase (ADH), urease (URE), citrate utilization (CIT), β-glucosidase (BGL), starch dyrolysis (AMD), L-arabinose fermentation (LAR), ribose fermentation (RIB), sorbitol fermentation (SOR), D-tagatose fermentation (DTA), N-acetyl-glucosamine fermentation (NAG), fructose fermentation (FRU), mannose fermentation (MAS), galactose fermentation (GAL), gentiobiose fermentation (GEN) and α-methyl-D-mannoside fermentation (MDM);

(12) the coding test items of identifying lactobacilli are 15 tests of arbutine fermentation (ARB), ribose fermentation (RIB), N-acetyl-glucosamine fermentation (NAG), D-xylose fermentation (DXY), trehalose fermentation (TRE), sorbitol fermentation (SOR), sucrose fermentation (SUC), lactose fermentation, (LAC), celloblose fermentation (CEL), melibiose fermentation (MEL), L-arabinose fermentation (LAR), rhamnose fermentation (RHA), D-tagatose fermentation (DTA), gluconate fermentation (GNT) and strach hydrolysis (AMD) and that the kind of bacteria biochemical properties-identifying papers that detect biological properties of bacteria according to the bacteria identification method are characterized in that the bacteria biochemical test mediums added in the paper-holes are one of the following 12 groups;

(1) the biochemical properties-identifying papers of parenteral gram-negative bacilli are assimilation test mediums of 2-keto-gluconate (2 KG), 3-hydroxy-benzoate (3 HB), 3-hydroxy-butyrate (OBU), citrate (CIT), L-proline (LPR), histose (HIS), N-acetyl-D-glucosamine (NAG), glycogen (GLY), maltose (MAL), sucrose (SUC), D-melibiose (MEL), L-fucose (FUC), D-glucose (GLU), inositol (INO) and manitol (MAN);

(2) the biochemical properties-identifying papers of enteric gram-negative bacilli are test mediums of lysine decarboxylas (LDC), ornithint decarboxylase (ODC), arginine dihydrolase (ADH), indole production (IND), urease (URE), citrate utilization (CIT), glucose oxidation (GLO), mannitol fermentation (MAN), sucrose fermentation (SUC), rhammose fermentation (RHA), amygdelin fermentation (AMY) and sorbitol fermentation (SOR);

(3) the biochemical properties-identifying papers of Enterobacteriaceae bacteria are test mediums of lysine decarboxylase (LDC), ornitine decarboxylase (ODC), malonate utilization (MAU), urease (URE), cellobiose fermentation (CEL), D-sorbitol fermentation (SOR), L-arabinose fermentation (LAR), adonitol fermentation (ADO), sucrose fermentation (SUC), dulcitol fermentation (DUL), α-methyl-D-glucoside fermentation (ANG) and D-mannitol fermentation (MAN);

(4) the biochemical properties-identifying papers of anaenobic bacteria are test mediums of α-glucosidase (AGL,), α-galactosidase (AGA), α-arabinosidase (AAR), β-glucosidase (BGL), β-galactosidase (BGA), β-glucuronidase (BGU), leucine anglamidase (LAA), proline arylamidase (PRA), alkaline phosphatase (ALP), indole production (IND), mannose fermentation (MAS) and N-acetyl-D-glucosaminidase (NAG);

(5) the biochemical properties-identifying papers of neisserial hemophilus are test mediums of growth in Martin-Thayer medium (MTM), glucose fermentation (GLU), maltose fermentation (MLT), β-glucosidase (BGL), phenylphosphonate (OPS), glycine arylamidase (GLY) Y-glutamyl arylamidase (GGT), proline arylamidase (PRO), and reduction of resazurin (RES);

(6) the biochemical properties-identifying papers of camylobacter are test mediums of catalase (CAT), reduction of intrate (NIT), urease (URE), succinate assimilation (SUT), acetate assimulation (ACE) hippurate hydrolysis (HIP), hydrogen sulfide production (HYS), Y-glutamyl transferase (GGT) and alkaline phosphatase (ALP);

(7) the biochemical properties-identifying papers of yeast-like fungi are assimilation test mediums of 2-keto-gluconate (2 KG), actidione (Act), erythritol (ERY), mannitol (MAN), inositol (INO), N-acetyl-glucosamine (NAG), L-arabinose (LAR), galactose (GAL), raffinose (RAF), cellobose (CEL), lactose (LAC), maltose (MAL), malibiose (MEL), trehalose (TRE) and esculin (ESC);

(8) the biochemical properties-identifying papers of corynebacteria are the mediums of redact of intrate (MI), urease (URE), esculin hydrolysis (ESC), L-maltose fermentation (MAL), sucrose fermentation (SUC), riborse fermentation (RIB), lactose fermentation (LAC), α-glucosidase (AGL), and β-galactosidase (BGA);

(9) the biochemical properties-identifying papers of micrococcaceae aceria are test medium of urease (URE), reduction of nitrate (NIT), 3-hydroxyl-butanone production (HYB), arginine dihyrolase (ADH), ornithinic decarboxylase (ODC), alkaline phosphatase (ALP), β-galactosidase (BGA), β-glucuronidase (BGU), glucose fermentation (GLF), sucrose fermentation (SUC), mannitol fermentation (MAN) and trehalose fermentation (TRE);

(10) the biochemical properties-identifying papers of Streptoccaceae bacteria are test mediums of 3-hydroxy-butanone production (HYB), hippurate hydrolysis (HIP), arginine dihydrolase (ADH), α-leucine arylamidase (LAA), b-glucuronidase (BGU), β-galactosidase (BGA), ribose fermentation (RIB), raffinose fermentation (RAF), sorbitol fermentation (SOR), L-arabinose fermentation (LAR) and trehalose fermentation (TRE);

(11) the biochemical properties-identifying papers of bacilli are test mediums of arginine dihydrolase (ADH), urease (URE), citrate utilization (CIT), β-glucosidase, (BGL), starch hydrolysis (AMD), L-arabinose fermentation (LAR), ribose fermentation (RIB), sorbitol fermentation (SOR), D-tagatose fermentation (DTA), N-acetyl-glucosamine fermentation (NAG), fructose fermentation (FRU), mannose fermentation (MAS), galactose fermentation (GAL), gentiobiose fermentation (GEN) and α-methyl-D-mannoside fermentation (MDM); and (12) the biochemical properties-identifying papers of lactobacilli are test mediums of arbutine fermentation (ARB), ribose fermentation (RIB), N-acetyl-glucosaine fermentation (NAG), d-xylose fermentation (DXY), trehalose fermentation (TRE), sorbitol fermentation (SOR), sucrose fermentation (SUC), lactose fermentation (LAC), cellobiose fermentation (CEL), melibiose fermentation (MEL), L-arabinose fermentation (LAR), rhamnose fermentation (RHA), D-tagotose fermentation (DTA), gluconate fermentation (GNT) and starch hydrolysis (AMD), said method comprising the steps of:

(a.) selecting the coding test items for bacteria identification according to known bacteria biological properties;

(b.) preparting bacteria biochemical property, identifying papers based upon the selected coding test items;

(c.) using the bacteria biochemical, identifying papers to detect the biochemical properties of the bacterial strain to be identified.

2. A bacteria identification apparatus using the bacteria identification method defined in claim 1 comprising:

image sampling unit, input unit, processing unit, storage unit, output unit and software system, characterized in that the storage unit use the non-volatile semi-conductor memory to store software and data.

3. An bacteria identification apparatus according to claim 2, characterized in that said non-volatile semiconductor memory is any one of programmable read-only memory, erasable-programmable read-only memory or flash memory.

4. An bacteria identification apparatus according to claim 2, characterized in that said output unit is color CRT or liquid crystal display, which can display biological properties of bacteria in the form of sketch image with the support of software.

5. An bacteria identification apparatus according to claim 2, characterized in that said image sampling unit has CCD camera and image sampling means; with the support of software, said CCD camera transfer color-changing image which embodies bacteria biological properties into video signal being transfered into image sampling means; said image sampling means transfers the video signal from CCD camera into digital signal to be processed by processing unit.

6. An bacteria identification apparatus according to claim 2, characterized in that said image sampling unit, input unit, processing unit, storage unit and output unit assembled together as a whole.

* * * * *